United States Patent [19]
Boykin et al.

[11] Patent Number: 5,602,172
[45] Date of Patent: Feb. 11, 1997

[54] METHODS OF INHIBITING *PNEUMOCYSTIS CARINII* PNEUMONIA, *GIARDIA LAMBLIA,* AND CRYPTOSPORIDIUM AND COMPOUNDS USEFUL THEREFOR

[75] Inventors: David W. Boykin, Atlanta, Ga.; Christine C. Dykstra, Chapel Hill, N.C.; Richard R. Tidwell, Pittsboro, N.C.; James E. Hall, Chapel Hill, N.C.; W. David Wilson; Arvind Kumar, both of Atlanta, Ga.; Byron L. Blagburn, Auburn, Ala.

[73] Assignees: The University of North Carolina at Chapel Hill, Chapel Hill, N.C.; Auburn University, Auburn, Ala.; Georgia State University Research Foundation, Inc., Atlanta, Ga.

[21] Appl. No.: 453,276

[22] Filed: May 30, 1995

Related U.S. Application Data

[63] Continuation of Ser. No. 339,487, Nov. 14, 1994, abandoned, which is a continuation-in-part of Ser. No. 238,766, May 6, 1994.

[51] Int. Cl.$^6$ ........................................... A61K 31/34
[52] U.S. Cl. ........................ 514/461; 514/471; 514/472
[58] Field of Search ........................... 514/461, 471, 514/472

[56] References Cited

PUBLICATIONS

Das, B. P., et al., 1,4–Bis(4–guanylphenylethyl)benzenes as Potential Antitrypanosomal Agents, *J. Pharmaceutical Sciences* 71:465 (1982).
Das, B. P., et al., Synthesis and Antiprotozoal Activity of 2,5–Bis(4–guanylphenyl)furans, *J. Medicinal Chemistry* 20:531 (1977).
Das, B. P. et al., Synthesis and Antiprotozoal Activity of 2,5–Bis(4–guanylphenyl)thiophenes and –pyrroles, *J. Medicinal Chemistry* 20:1219 (1977).
Das, B. P., et al., Synthesis and Antitrypanosomal Activity of Some Bis(4–guanylphenyl) Five– and Six–Membered Ring Heterocycles, *J. Medicinal Chemistry* 23:578 (1980).
Dykstra, C., et al, Synthesis and Characterization of a Novel Series of Aromatic Dicationic Furans With DNA–Specific Fluorescence Properties, pp. 1–7, (1994).
Rooney et al., *Human Cytogenetics: A Practical Approach*, ed., IRL Press, Oxford University Press, selected pages.
Steck, E. A., et al., *Trypanosoma rhodesiense*: Evaluation of the Antitrypanosomal Action of 2,5–bis(4–Guanylphenyl)furan Dihydrochloride, *Experimental Parasitology* 53, pp. 133–144 (1982).
Das et al J Med Chem vol. 20(9) pp. 1219–1221—1972.
Das et al J. Pharm Sci vol. 71(4) 1982 pp. 465–466.
Das et al J Med Chem vol. 20(4) pp. 531–536.
Parasitology vol. 105 Supplement 1992 pp. S94–S101.

*Primary Examiner*—Russell Travers
*Attorney, Agent, or Firm*—Bell, Seltzer, Park & Gibson

[57] ABSTRACT

The present invention provides methods for treating *Pneumocystis carinii* pneumonia, *Giardia lamblia*, and *Cryptosporidium parvum* in a subject in need of such treatment. The methods comprise adminstering to the subject a compound of Formula (I):

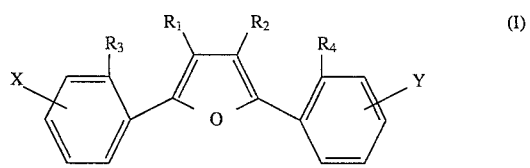

wherein:

$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;

$R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

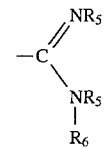

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof. The compounds ar administered in an amount effective to treat the condition. The present invention also includes novel compounds useful in the treatment of *Pneumocystis carinii* pneumonia, *Giardia lamblia*, and *Cryptosporidium parvum*.

19 Claims, No Drawings

METHODS OF INHIBITING *PNEUMOCYSTIS CARINII* PNEUMONIA, *GIARDIA LAMBLIA*, AND CRYPTOSPORIDIUM AND COMPOUNDS USEFUL THEREFOR

The present invention was made with Government support under Grant Number UO1-A1-3363 from the National Institutes of Health. The Government has certain rights to this invention.

RELATED APPLICATIONS

This application is a continuation of Ser. No. 08/339,487 filed Nov. 14, 1994, now abandoned, which is a continuation-in-part of U.S. patent application Ser. No. 08/238,766 filed 6 May 1994.

FIELD OF THE INVENTION

The present invention relates to methods of combatting *Pneumocystis carinii* pneumonia with dicationic compounds. Specifically, the present invention relates to methods of combatting *Pneumocystis carinii* pneumonia with bis-aryl furans and novel bis-aryl furans useful therefor.

BACKGROUND OF THE INVENTION

Pentamidine is used for the treatment of *Pneumocystis carinii* pneumonia, or "PCP". The importance of pentamidine has escalated recently due to the marked increase of patients suffering from PCP. The increase in the afflicted patient population is an unfortunate consequence of the increasing presence of Acquired Immunodeficiency Syndrome ("AIDS"). It is now estimated that approximately 70 percent of AIDS patients contract PCP. Because of the high incidence of PCP in AIDS patients, pentamidine has found utility not only in the treatment of PCP, but also as prophylaxis, in preventing or delaying the initial onset or recurrence of PCP, especially in AIDS patients. Currently, pentamidine is most commonly administered as a therapeutic agent by intravenous infusion and as a prophylactic agent by aerosol dosage.

However, an unfortunate side effect of pentamidine is its toxicity. Some fatalities have been attributed to severe hypotension, hypoglycemia, and cardiac arrhythmias in patients treated with pentamidine. Contrawise, insufficient dosage may result in dissemination of disease beyond the lung, an occurrence of which is associated with a poor prognosis.

Pentamidine is presently in limited use because of cost and toxicity. Therapeutic drug monitoring is not used because of the cost and complexity of the currently available assay techniques which require the extraction of plasma and High Performance Liquid Chromatography analysis. As a result, the toxicity of pentamidine is a significant concern, which is driving the market toward the development of pentamidine substitutes capable of avoiding or minimizing the undesirable side effects associated with the use of pentamidine. Accordingly, it is an object of the present invention to provide new methods of treating *Pneumocystis carinii* pneumonia.

SUMMARY OF THE INVENTION

As a first aspect, the present invention provides a method of treating *Pneumocystis carinii* pneumonia. The method includes administering to a subject in need of such treatment, an amount effective to treat *Pneumocystis carinii* pneumonia of a compound of Formula (I):

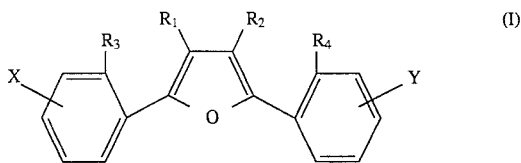

wherein:

$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;

$R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

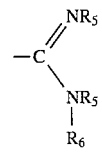

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl.

In another embodiment, two $R_5$ groups together represent

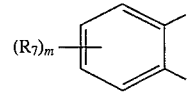

wherein m is from 1–3 and $R_7$ is H or —$CONHR_8NR_9R_{10}$, wherein $R_8$ is loweralkyl, and $R_9$ and $R_{10}$ are each independently selected from the group consisting of H and loweralkyl, although these compounds are not currently preferred.

As a second aspect, the present invention provides compounds useful for the treatment of *Pneumocystis carinii* pneumonia. The compounds have the structural Formula (I), described above. In particular, novel compounds useful for the treatment of *Pneumocystis carinii* pneumonia include compounds defined wherein X and Y are located in the para position and are each

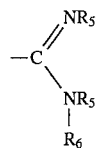

and wherein:

(a) $R_1$ is H, $R_2$ is H or loweralkyl, $R_3$ is H, $R_4$ is H, $R_5$ is H, and $R_6$ is isoalkyl, such as isopropyl, isobutyl, isopentyl, and the like;

(b) $R_1$ is H, $R_2$ is H, $R_3$ is H, $R_4$ is H, $R_5$ is H, and $R_6$ is $C_3$-$C_8$ alkoxyalkyl;

(c) $R_1$ is H, $R_2$ is H or loweralkyl, $R_3$ is H, $R_4$ is H, $R_5$ is H, and $R_6$ is alkylhydroxy, such as ethylhydroxy, propylhydroxy, butylhydroxy, pentylhydroxy, and hexylhydroxy;

(d) $R_1$ is H, $R_2$ is H or loweralkyl, $R_3$ is H, $R_4$ is H, $R_5$ is H, and $R_6$ is propoxyethyl;

(e) $R_1$ is H, $R_2$ is H or loweralkyl, $R_3$ is H, $R_4$ is H, $R_5$ is H, and $R_6$ is propoxyisopropyl;

(f) $R_1$ is H, $R_2$ is H or loweralkyl, $R_3$ is H, $R_4$ is H, $R_5$ is H, and $R_6$ is aryl or alkylaryl; and (g) $R_1$ is H, $R_2$ is H or loweralkyl, $R_3$ is H, $R_4$ is H, $R_5$ is H, and $R_6$ is alkylcycloalkyl; and pharmaceutically acceptable salts thereof.

As a third aspect, the present invention provides a method of treating *Giardia lamblia* in a patient in need of such treatment. The method includes administering to a patient in need of such treatment, a compound of Formula (I) above, in an amount effective to treat *Giardia lamblia*. Novel compounds useful for treating *Giardia lamblia* are also disclosed.

As a fourth aspect, the present invention provides a method of treating *Cryptosporidium parvum* in a patient in need of such treatment. The method includes administering to a patient in need of such treatment, a compound of Formula (I) above, in an amount effective to treat *Cryptosporidium parvum*. Novel compounds useful for treating *Cryptosporidium parvum* are also disclosed.

The foregoing and other objects and aspects of the present invention are explained in detail in the specification set forth hereinbelow.

DETAILED DESCRIPTION OF THE INVENTION

The term "loweralkyl," as used herein, refers to $C_1$-$C_6$ linear or branched alkyl, such as methyl, ethyl, propyl, butyl, isopropyl, sec-butyl, tert-butyl, pentyl, isopentyl, and hexyl. Isoalkyl groups, such as isopropyl, isobutyl, isopentyl, and the like are currently preferred. The term "loweralkoxy" or "oxyalkyl" as used herein, refers to $C_1$-$C_6$ linear or branched alkoxy, such as methoxy, ethoxy, propyloxy, butyloxy, isopropyloxy, and t-butyloxy. Methoxy is currently preferred.

As noted above, the methods of the present invention are useful for treating *Pneumocystis carinii* pneumonia, *Giardia lamblia*, and *Cryptosporidium parvum*. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects although the methods of the present invention may be useful with any suitable subject known to those skilled in the art. As noted above, the present invention provides pharmaceutical formulations comprising the aforementioned compounds of Formula (I), or pharmaceutically acceptable salts thereof, in pharmaceutically acceptable carriers for aerosol, oral, and parenteral administration as discussed in greater detail below. Also, the present invention provides such compounds or salts thereof which have been lyophilized and which may be reconstituted to form pharmaceutically acceptable formulations for administration, as by intravenous or intramuscular injection.

Obviously, the therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the condition is essentially controlled. Lower doses given less frequently can be used to prevent or reduce the incidence or recurrence of the infection.

In accordance with the present method, a compound of Formula (I), or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the compounds of Formula (I) also provide a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As *Pneumocystis carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula (I) or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immunocompromised patient who has never experienced an episode of *Pneumocystis carinii* pneumonia. In this respect, a patient who has been diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula (I) or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula (I), or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula (I) or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula (I), or salts thereof, such as aqueous base emulsions. In such an instance, the composition will contain a sufficient amount of pharmaceutically acceptable emulsifying agent to emulsify the desired amount of the compound of Formula (I) or salt thereof. Particularly useful emulsifying agents include phosphatidyl cholines, and lecithin.

Further, the present invention provides liposomal formulations of the compounds of Formula (I) and salts thereof. The technology for forming liposomal suspensions is well known in the art. When the compound of Formula (I) or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula (I) or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula (I) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula (I), or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula (I) or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/ml, or greater. Also, as used in the present specification, the term "water-insoluble" is meant to define any composition which has solubility in water of less than about 20 mg/ml. For certain applications, water soluble compounds or salts may be desirable whereas for other applications water-insoluble compounds or salts likewise may be desirable.

The compounds of Formula (I) above which are particularly preferred for the methods of treating *Pneumocystis carinii* pneumonia, *Giardia lamblia*, and *Cryptosporidium parvum* include a variety of compounds. For example, particularly preferred compounds are defined by Formula (I) wherein X and Y are each

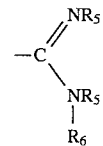

and (a): $R_1$ is H, $R_2$ is H, $R_3$ is H, $R_4$ is H, $R_5$ is H, and $R_6$ is H, alkyl, hydroxyalkyl, aminoalkyl, alkylamino, or alkylaminoalkyl; (b): $R_1$ is H or loweralkyl, $R_2$ is loweralkyl, $R_3$ is H, $R_4$ is H, $R_5$ is H, and $R_6$ is H or loweralkyl; (c): $R_1$ is H or oxyalkyl, $R_2$ is H, oxyalkyl, or oxyarylalkyl, $R_3$ is H, $R_4$ is H, two $R_5$ groups together represent $C_2$ alkyl, and $R_6$ is H, loweralkyl or hydroxyalkyl; (d): $R_1$ is H, $R_2$ is H or oxyarylalkyl, $R_3$ is H, $R_4$ is H, two $R_5$ groups together represent $C_3$ alkyl, and $R_6$ is H; (f): $R_1$ is H, $R_2$ is H, $R_3$ is H, $R_4$ is H, two $R_5$ groups together represent

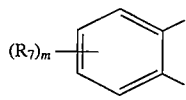

wherein m is 1, and $R_7$ is H or —$CONHR_8NR_9R_{10}$, wherein $R_8$ is loweralkyl, and $R_9$ and $R_{10}$ are each H, and $R_6$ is H; and (e): $R_1$ is H, $R_2$ is H, $R_3$ is H, $R_4$ is H, two groups $R_5$ groups together represent $C_4$ alkyl, and $R_6$ is H.

Examples of compounds exemplary of Formula (I) above include, but are not limited to:

2,5-bis(4-guanylphenyl)furan, 2,5-bis(4-guanylphenyl)-3,4-dimethylfuran, 2,5-di-p[2(3,4,5,6-tetrahydropyrimidyl)phenyl]furan, 2,5-bis[4-(2-imidazolinyl)phenyl]furan, 2,5-[bis{4-(2-tetrahydropyrimidinyl)}phenyl]-p(tolyloxy)furan, 2,5-[bis{4-(2-imidazolinyl)}phenyl]3-p(tolyloxy)furan, 2,5-bis{4-[5-(N-2-aminoethylamido)benzimidazol-2-yl]phenyl}furan, 2,5-Bis[4-(3a,4,5,6,7,7a-hexahydro-1H-benzimidazol-2-yl)phenyl]furan, 2,5-bis[4-(4,5,6,7-tetrahydro-1H-1,3-diazepin-2-yl)phenyl]furan, 2,5-bis(4-N,N-dimethylcarboxhydrazidephenyl)furan, 2,5-bis{4-[2-(N-2-hydroxyethyl)imidazolinyl]-phenyl}furan, 2,5-bis[4-(N-isopropylamidino)phenyl]furan, 2,5-bis {4-[3-(dimethylaminopropyl)amidino]phenyl}furan, 2,5-bis-{4-[N-(3-aminopropyl)amidino]phenyl}furan, 2,5-bis[2-(imidzaolinyl)phenyl]-3,4-bis(methoxymethyl)-furan, 2,5-bis[4-N-(dimethylaminoethyl)guanyl]phenylfuran, 2,5-bis-{4-[(N-2-hydroxyethyl)guanyl]phenyl}furan, 2,5-bis-[4-N-(cyclopropylguanyl)phenyl]furan, 2,5-bis-[4-(N,N-diethylaminopropyl)guanyl]phenylfuran, 2,5-bis-{4-[2-(N-ethylimidazolinyl)]phenyl}furan, 2,5-bis-{4-[N-(3-pentylguanyl)]}phenylfuran, 2,5-bis-[4-(2-imidazolinyl)phenyl]-3-methoxyfuran, 2,5-bis[4-(N-isopropylamidino)phenyl]-3-methylfuran, and the pharmaceutically acceptable salts thereof.

Compounds employed in carrying out the present invention may be prepared in accordance with techniques known to those skilled in the art (see, e.g., B. P. Das, et al., Synthesis and antiprotozoal activity of 2,5-Bis(4-guanylphenyl) furans, *J. Med. Chem.* 20:531 (1977), the disclosure of which is incorporated herein by reference in its entirety), particularly in light of the disclosure and examples set forth below.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, in solution. After the reaction is complete, the salts are crystallized from solution by the addition of an appropriate amount of solvent in which the salt is insoluble.

Methods of combating *Giardia lamblia* with the compounds of Formula (I) above are carried out in essentially the same manner as given above, and pharmaceutical formulations of the compounds of Formula (I) for combating *Giardia lamblia* are prepared in essentially the same manner as given above.

Methods of combating *Cryptosporidium parvum* with the compounds of Formula (I) above are carried out in essentially the same manner as given above, and pharmaceutical formulations of the compounds of Formula (1) for combating *Cryptosporidium parvum* are prepared in essentially the same manner as given above.

The compounds of the present invention are useful not only in methods for treating *Pneumocystis carinii* pneumonia, *Giardia lamblia*, and *Cryptosporidium parvum*, but also in methods of inhibiting enzymes such as topoisomerase. The compounds of Formula (I) are particularly useful for inhibiting topoisomerase II. See, S. Doucc-Racy, et al., *Proc. Natl. Acad. Sci.* USA 83:7152 (1986).

As noted above, the compounds useful in the methods of the present invention may be prepared according to techniques known in the art. According to one method, the compounds of Formula (I) can be prepared by: (a) cyclodehydrative furanization of 1,4-diketones according to the procedure taught by R. E. Lutz, et al., *J. Am. Chem. Soc.* 56:2698 (1934) to form 2,5-bis-(4-bromophenyl) furan; (b) nitrilization of 2,5-bis(4-bromophenyl) furan using copper (I) cyanide to produce the corresponding bis-nitrile 2,5-bis-(4-cyanophenyl) furan; and (c) conversion of the bis-nitrile to the desired bis-dicationic aryl furan of Formula (I). This method is illustrated in Scheme 1 below.

Scheme 1

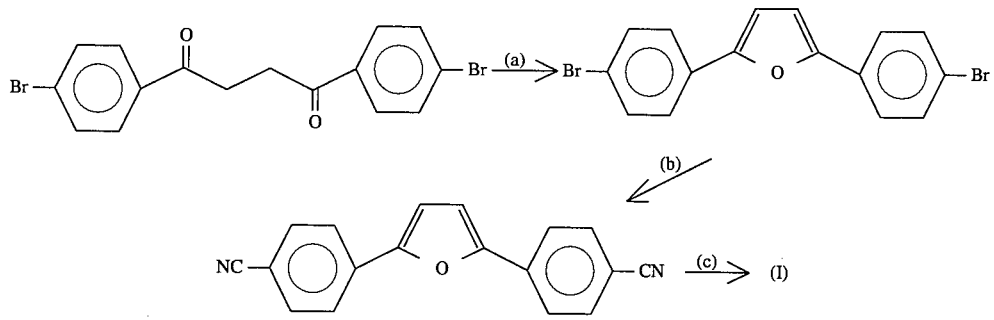

According to a second method, compounds of Formula (I) may be prepared by (a) converting the appropriate bromoacetophenone to the ethyl bromophenyl-oxopropionate using sodium hydride and diethylcarbonate in tetrahydrofuran, (b) converting the ethyl bromophenyl-oxopropionate to the ethyl bis-bromobenzoylpropionate using bromophenacyl bromide, (c) converting the bis-bromobenzoylpropionate to the ethyl bis-bromophenyl furan using ethanol and hydrochloric acid, (d) hydrolysis of the ethyl bis-bromophenyl furan to the bis-bromophenyl furan carboxylic acid using potassium hydroxide followed by hydrochloric acid, (e) converting the carboxylic acid to the corresponding bis-nitrile with copper (I) cyanide and heat, and converting the bis-nitrile to the appropriate bis-dicationic aryl furan. This method is illustrated in Scheme 2 below.

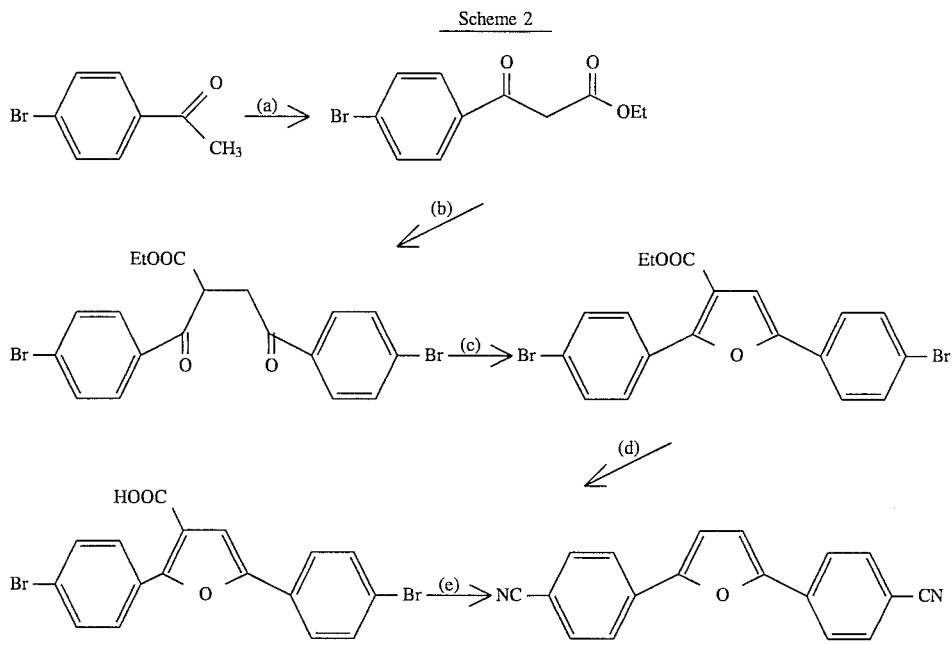

Scheme 2

Conversion of the bis-nitrile to the bis-dicationic aryl furan of Formula (I) may be accomplished according to several methods known to those skilled in the art. According to one currently preferred method, conversion of the bis-nitrile to the bis-dicationic aryl furan is carried out by conversion into intermediate imidate esters using classical Pinner methodology, followed by reaction of these intermediates with ammonia or the appropriate diamine for example, ethylenediamine, 1,3-propanediamine, etc., as exemplified in the Examples set forth below. According to a second currently preferred method, the bis-nitrile is converted to the bis-dicationic aryl furan by fusion of the bis-nitrile directly with the hydrochloride salt of the appropriate diamine by thermolysis. This technique is particularly useful for the preparation of compounds wherein two $R_5$ groups together form a cyclic alkyl.

The present invention is explained in greater detail in the following examples. As used herein, "mp" means melting point, "NMR" means nuclear magnetic resonance, "MHz" means megahertz, "FAB" means fast atomic bombardment, "EI" means electron ionization, "IR" means infrared spectra, "MS" means mass spectroscopy, "Hz" means hertz, "g" means grams, "ml" means milliliters, "L" means liters, "hr" means hours, "° C." means degrees Centigrade, "DMSO" means dimethyl sulfoxide, "DMF" means dimethyl formamide, and "m/e" means mass divided by charge. These Examples are illustrative and are not to be taken as limiting of the invention.

Melting points are recorded using a Thomas Hoover (Uni-Melt) capillary melting point apparatus and are uncorrected. $^1$H NMR and $^{13}$C NMR spectra are recorded employing a Varian GX400 spectrometer and chemical shifts. (δ) are in ppm relative to TMS unless otherwise noted. Mass spectra are recorded on a VG Instruments 70-SE spectrometer. IR spectra are recorded using a Michelson 100 instrument.

EXAMPLE 1

Preparation of Precursor Compounds 2,5-Bis(p-bromophenyl)furan. A literature procedure as known in the art for preparation of trans-di-p-bromobenzoylethylene from bromobenzene and fumaryl chloride was employed. J. B. Conant and R. E. Lutz, *J. Am. Chem. Soc.* 47, 881 (1925). The ethylene compound was reduced with Zn-HOAc to prepare 1,4-di-p-bromophenyl-1,4-butanedione. E. Campaigne and W. O. Foye, *J. Org. Chem.* 17, 1405 (1952). The saturated 1,4-diketone (7.9 g, 0.02 mol) was suspended in 80 ml of AC$_2$O and the mixture was heated to reflux. Concentrated H$_2$SO$_4$(4–5 drops) was added and refluxing was continued for 5 min. The solution was poured into water-ice (1 L), stirred well, and filtered: crude yield 7 g (93%). Recrystallization from acetic acid gave 5.6 g (75%), mp 198°–199° C. (lit. (R. E. Lutz and W. M. Eisner, *J. Am. Chem. Soc.* 56, 2698 (1934)) mp 200°–201 ° C.).

2,5-Bis(p-cyanophenyl)furan. A mixture of 7.5 g (0.02 mol) of 2,5-bis-(4-bromophenyl)furan and 4 g (0.045 mol) of Cu(CN) in 45 ml of quinoline was refluxed for 2 h. The mixture was poured into 300 ml of dilute HCl solution (caution, HCN is liberated) and filtered. The solid was washed with H$_2$O dilute NaOH, dilute HCl, and again with H$_2$O. The solid bis-nitrile was dissolved in acetone, filtered to remove inorganic residue, and passed through a short alumina column to remove traces of copper salts. The copper salts must be removed since they carry over to the bis-amidines from which they are difficult to purify. A convenient method to detect the presence of copper salts is a flame test. Evaporation of the eluent from the alumina column and recrystallization from ethanol gave 3.5 g (65%), mp 294°–295° C.

EXAMPLE 2

Preparation of 2,5-Bis(4-amidinophenyl)furan dihydrochloride 2,5-Bis(4-cyanophenyl)furan (3 g, 0.011 mol) (prepared as described in Example 1) in a mixture of 100 ml of dioxane and 25 ml of absolute ethanol was saturated with dry HCl gas at 5° C. The solution was placed in a pressure bottle and shaken for 3 days (room temperature). An intermediate product, an imidate ester hydrochloride, precipitated as a yellow solid, was filtered and dried under vacuum at room temperature overnight. The IR spectra of the imidate ester hydrochloride was free of adsorption for nitrile and it was used directly without further characterization. A suspension of the imidate ester hydrochloride (3.5 g) in 100 ml of absolute ethanol was saturated at 5° C. with anhydrous ammonia. The suspension (pressure bottle) was shaken for 3 days at room temperature. The reaction mixture was filtered and the solid was dried and dissolved in warm absolute ethanol (ca. 1.5 L). The solution was acidified with anhydrous HCl at 5° C., concentrated under vacuum at room temperature, and 2.5 g (60%) of yellow crystals were obtained. Recrystallization from absolute ethanol gave mp 400°–401 ° C. dec.

EXAMPLE 3

Preparation of 2,5-Bis[4-(4,5-dihydro-1H-imidazol-2-yl)phenyl]furan

A solution of an imidate ester hydrochloride intermediate synthesized as described in Example 2, 2,1 g (0.005 mol), and 0.6 g (0.01 mol) of ethylenediamine in 50 ml of absolute ethanol was refluxed overnight. The solid which formed was filtered and recrystallized from absolute ethanol saturated with anhydrous HCl to yield 2,5-Bis[4-(2-imidazolinyl)phenyl]furan, 1.9 g (90%), mp 409°–410° C. dec.

EXAMPLE 4

Preparation of 2,5-Bis[4-(4,5-dihydro-1H-imidazol-2-yl)phenyl]furan dihydrochloride dihydrate Bis-nitrile (0.5 g, 1.9 mmole), ethylenediamine dihydrochloride (4.9 g, 37 mmole), ethylenediamine (2.5 ml, 37 mmole) are mixed. The mixture is heated at 300°–310° C. for 10 minutes in a sand bath. After cooling the mixture is dissolved in hot water. Yellow crystals separate on cooling. The compound is recrystallized from boiling water to yield 208 mg (24%), and then dried under vacuum at 80° C for 12 hr. TLC ($CHCl_3:CH_3OH:25\% \ NH_4OH=11:4:1$, one spot), mp>360° C. Analysis calculated for $C_{22}H_{20}N_4O.2HCl.2H_2O$: C:56.78, H:5.60, N:12.04; found: C:56.69, H:5.63, N:12.07. $^1$H-NMR (DMSO-$d_6$, TMS), 4.01 (s, 8H), 7.45 (s, 2H), 8.08 (d, 4H, J=8.3 Hz), 8.15 (d, 4H, J=8.3 Hz), 8.15 (d, 4H, J=8.3 Hz), 10.50 (brs, 4H). $^{13}$C-NMR (DMSO-$d_6$, TMS), δ 45.5, 113.2, 121.6, 125.3, 130.1, 135.8, 141.3, 153.4, 165.8. IR (KBr): 3412, 3123, 2971, 1608, 1580, 1491, 1367, 1287, 1033, 850, 745, 673 cm$^{-1}$. MS m/e 356 (free base).

EXAMPLE 5

Preparation of 2,5-Bis[4-(1,4,5,6-tetrahydropyrimidin-2-yl)phenyl]furan

In a similar manner as set forth in Example 3, an imidate ester hydrochloride synthesized as described above in Example 2 was reacted with 1,3-propanediamine to yield (90%) of the 2,5-Bis[4-(1,4,5,6-tetrahydropyrimidin-2-yl)phenyl]furan, mp 430°–431° C. dec.

EXAMPLE 6

Preparation of 2,5-Bis[4-(4,5,6,7-tetrahydro-1H-1,3-diazepin-2-yl) phenyl]furan dihydrochloride The bis-methoxyethanol imidate ester (1 g, 0.002 mole), 1,4-diaminofurane (0.5 g) in 10 ml of 1,2-dimethoxyethane are refluxed for 2 days. The solvent is removed under vacuum and water is added. The precipitate is filtered, washed with water, and dried in vacuum oven (top>300° C.). The filtrate is neutralized using 2M sodium hydroxide and another portion of the free base is obtained. The crude free base is converted into the hydrocholride (mp>300° C.) by hydrogen chloride in methanol. The total yield of free base is 51%. Analysis calculated for $C_{26}H_{28}N_4O.2HCl.3.5H_2O$ (548.50): C:56.93, H:6.80, N:10.22; found: C:56.99, H:6.80, N:10.26. $^1$H-NMR (DMSO-$d_6$) δ 2.02 (s, 8H), 3.71 (s, 8H), 7.38 (s, 2H), 7.86 (d, 4H, J=8.3 Hz), 8.04 (d, 4H, J=8.3 Hz), 9.77 (s, 4H). $^{13}$C-NMR ($D_2O$ ($CH_3)_3SiCH_2CH_2CO_2Na$), δ 28.0, 47.0, 113.9, 126.5, 129.7, 131.2, 137.0, 154.5, 167.1. IR (KBr), 687, 747, 814, 930, 1131, 1364, 1459, 1597, 3008, 3164 cm$^{-1}$. MS (EI) m/e 412 (free base).

EXAMPLE 7

Preparation of 2,5-Bis[4-(3a,4,5,6,7,7a-hexahydro-1H-benzimidazol-2-yl)phenyl]furan dihydrochloride 1,2-Diaminocyclohexane (9 ml) is treated with ethanolic HC. The solution is evaporated to dryness and a new portion of the amine (9 ml), and 2,5-bis-(4-cyanophenyl)furan (2 g) is added. The mixture is maintained at 300°–310° C. in a sand bath for about 10 min. Progress of the reaction is monitored by TLC ($CHCl_3:CH_3OH:NH_4OH=44:8:1$, v/v/v). After cooling the residue is recrystallized from water to afford analytically pure yellow crystals (1.4 g, 36%), having an mp>300° C. Analysis calculated for $C_{30}H_{32}N_4O.2HCl.0.25H_2O$: C:66.48, H:6.42, N:10.34; found: C:66.47, H:6.40, N: 10.30. $^1$H-NMR (DMSO-$d_6$, TMS), δ 1.30–2.00 (m, 16H), 4.36 (s, 4H), 7.46 (s, 2H), 8.18 (m, 8H), 10.87 (s, 4H). $^{13}$C-NMR (DMSO-$d_6$, $D_2O$) α 18.9, 25.8, 57.0, 112.7, 122.3, 125.0, 130.0, 135.5, 153.4, 164.9. IR (KBr) 3413, 2991, 1597, 1501, 1354, 1293, 1016, 930, 853, 796, 747, 676 cm$^{-1}$. MS m/e 464 (free base).

EXAMPLE 8

Preparation of 2,5-Bis[4-(4,5-dihydro-1-(hydroxyethyl-1H-imidazol-2-yl)phenyl]furan dihydrochloride dihydrate A mixture of N-(2-hydroxyethyl)ethylene diamine (0.64 g, 0.006 mole) in 15 ml absolute ethanol and the imidate ester (0.87 mole, 0.002 mole) is heated under reflux for 12 hr. The solvent is removed by distillation, and the resulting residue is triturated with ice/water, the pH is adjusted to 10 with 2M NaOH and the precipitated solid is filtered, washed with water, dried, and recrystallized from ethanol-ether to yield a light yellow crystalline solid 0.72 g (81%) having an mp of 119°–120° C. IR(KBr) 3390, 3290, 3132, 2864, 1615, 1595, 1421, 1276, 1059, 849 cm$^{-1}$. $^1$H-NMR (DMSO-$d_6$) δ 7.87 (d, 4H, J=8.3), 7.64 (d, 4H, J=8.3), 7.16 (s, 2H), 3.75 (t, 4H, J=9.8), 3.53 (t, 4H, J=5.8) 3.47 (t, 4H, J=9.8), 3.1 (t, 4H, J=5.8). $^{13}$C-NMR (DMSO-$d_6$) δ 165.8, 152.4, 130.8, 128.7, 123.1, 109.2, 59.3, 52.6, 51.4, 51.1. MS m/e 444.

The free base 0.45 g (0.001 mole) is suspended in 10 ml ethanolic HCl and heated under reflux for 30 min, concentrated in vacuum, and triturated with dry ether to yield a shining yellow crystalline. The solid is filtered, washed with ether, and dried in vacuum to yield 0.45 g (89%) having an mp 178°–179° C. IR(KBr)3407, 3089, 2919, 1615, 1569, 1370, 1288, 1067, 853, 669 cm$^{-1}$. $^1$H-NMR (DMSO-d$_6$/50° C.) δ 10.8 (brs, 2H), 8.9 (d, 4H, J=8.6), 7.87 (d, 4H, J=8.6), 7.4 (s, 2H), 5.45 (vbr, 2H), 4.18–4.10(m, 4H), 3.99–3.92 (m, 4H), 3.66—3.5 (m, 4H), 3.48–3.42 (m, 4H). $^{13}$C-NMR (DMSO-d$_6$/50° C.) δ 165.9, 152.3, 133.4, 129.8, 123.7, 121.5, 111.2, 56.6, 49.4, 49.2, 42.5. Analysis calculated for C$_{26}$H$_{28}$N$_4$O$_3$.2HCl .H$_2$O: C:61.80, H:6.38, N: 11.09; found: C:61.62, H:6.51, N:10.89.

EXAMPLE 9

Preparation of 2,5-Bis[4-(4,5-dihydro-1-(ethyl)-1H-imidazol-2-yl)phenyl]furan dihydrochloride dihydrate To a suspension of the imidate ester (0.65 g, 0.0015 mole) in 10 ml absolute ethanol is added N-ethylethylene diamine (0.4 g, 0.0045 mole), and the mixture is heated at reflux under nitrogen for 12–14 hr. The solvent is removed by distillation under vacuum, the remaining oil was diluted with ice-water and basified with 1M NaOH to pH 10. A gummy solid separates from the aqueous phase. The solid is washed with water, dried in vacuum, and recrystallized from ethanol:CHCl$_3$ to yield a hygroscopic yellow solid, 0.45 g (73%). MS m/e 412. The free base (0.41 g, 0.001 mole) is dissolved in 10 ml ethanolic HCl and stirred at 35°–40° C. for 1 hr. The excess solvent is distilled under vacuum and the resulting semi-solid was triturated with dry ether. The ether was removed under vacuum and the resulting solid was dried under vacuum to yield a very hygroscopic yellow crystalline solid 0.45 g (93%) having an mp 163°–4° C. $^1$H NMR (D$_2$O/DMSOd$_6$) δ 8.08 (d, 4H, J=8.3), 7.76 (d, 4H, J=8.3), 7.26 (s, 2H), 4.24–4.06 (m, 8H), 3.6–3.56 (m, 4H), 1.34 (brt, 6H). $^{13}$C NMR (D$_2$O/DMSOd$_6$) δ 165.0, 154.2, 133.5, 129.3, 123.9, 121.3, 111.3, 48.9, 42.5, 41.7, 12.4. Analysis calculated for C$_{26}$H$_{28}$N$_4$O.2HCl.H$_2$O: C:61.17, H:6.32, N:10.97; found: C:60.93, H:6.44, N:10.85.

EXAMPLE 10

Preparation of 2,5-Bis{[4-(N-isopropyl)-amindino]phenyl}furan

Dry isopropylamine (0.47 g, 0.008 mole) was added to a suspension of an imidate ester as described in Example 2 (1.3 g, 0.003 mole) in 45 ml absolute ethanol. Within 0.5 hr the imidate ester dissolved and the mixture of the imidate ester and isopropylamine became colored. After ca. 3 hr a white solid precipitated; the slurry was stirred overnight at room temperature. The solvent was removed under reduced pressure, diluted with water, filtered and washed with water. After the solid was dried, it was recrystallized from an ethanol/ether mixture to yield a white solid 0.9 g (78%); mp 233°–4° C., $^1$H NMR (DMSO-d$_6$/60° C.) 7.79 (brs, 8H), 7.11 (s, 2H), 6.25 (br, 4H, 3.81 (br, 2H), 1.14 (6H, J=5.9) $^{13}$C NMR (DMSO-d$_6$/60° C.) 152.4, 142.0, 136.6, 130.4, 126.8, 122.8, 108.7, 43.5, 22.8.

EXAMPLE 11

Preparation of 2,5-Bis[4-N-isopropyl)amindino)phenyl] furan dihydrochloride

The free base (0.78 g, 0.002 mole) prepared as described in Example 10 was dissolved in 10 ml absolute ethanol and treated with 10 ml of ethanol saturated with hydrogen chloride and warmed for 2 hr. The mixture was reduced in volume to 5 ml. Addition of 20 ml of dry ether produced a bright yellow precipitate which was filtered, washed with 3×5 ml dry ether and dried in vac. at 65° C. for 2 hr to yield 0.8 g (87%). Mp 276°–7° C.(dec). IR (KBr). $^1$H NMR (DMSO-d$_6$) 9.72 (s, 1H) 9.69 (s, 1H), 9.57 (s, 2H), 9.24 (s, 2H), 8.06 (d, 4H, J=8.1), 7.86 (d, 4H, J=8.1), 7.42 (s, 2H), 4.14 (s, 2H, J=6.6), 1.29 (d, 12H, J=6.6). $^{13}$C NMR (DMSO-d$_6$) 161.1, 152.3, 133.6, 129.2, 127.7, 123.5, 111.3, 45.1, 21.1.

Anal. Calculated for: C$_{24}$H$_{28}$N$_4$O.2HCl.1.25 H$_2$O: C, 59.57; H, 6.79; N, 11.57. Found: C, 60.00; H, 6.80; N, 11.52.

EXAMPLE 12

Preparation of 2,5-bis[(4-(4,5-dihydro-1H-imidazol-2-yl)phenyl)]-3-(4-tolyloxy) furan 1-(4-tolyloxyl)-1,2-bis(4-bromobenzoyl)ethylene. To a solution of 1,2-dibromo-1,2-di(4-bromobenzoyl)ethane (11.1 g, 0.02 mole) in 35 ml of THF was added a suspension of sodium 4-methyl phenoxide [prepared from 0.92 g (0.04 mole) Na and 4.32 g (0.04 mole) 4-methylphenol in 30 ml THF by refluxing for 4–5 hr]. The yellow mixture was refluxed for 2–3 hr (TLC followed) after which the THF was removed under reduced pressure. The residue was treated with water, and the solid was filtered, washed with water, dried (Na$_2$SO$_4$), and dissolved in chloroform. The chloroform solution was passed through a silica column (elution with 2–5% ether in hexane). The result was an off white crystalline solid, 4.95 g (50%), mp 137°–8° C. IR (KBr) 3087, 3035, 2868, 1687, 1646, 1587, 1572, 1557, 1502, 1399, 1364, 1194, 1068, 1009, 971, 876, 815, 772, 526. $^1$H NMR (CDCl$_3$/35° C.) 7.92 (d, 2H, J=8.8), 7.65 (d, 2H, J=8.8), 7.55 (d, 2H, J=8.8), 7.48 (d, 2H, J=8.8), 7.27 (d, 2H, J=8.3), 7.11 (d, 2H, J=8.3), 6.32 (s, 1H), 2.4 (s, 3H). $^{13}$C NMR (CDCl$_3$/35° C.) 189.4, 187.6, 168.4, 150.9, 136.6, 136.0, 133.4, 132.3, 131.8, 130.9, 130.3, 129.6, 129.2, 128.2, 120.6, 101.8, 20.95. MS m/e 500 (M$^+$).

2,5-bis(4-Bromophenyl)-3-(p-tolyloxy)furan. A solution of 5.0 g (0.01 mole) 1-(4-tolyloxy)-1,2-bis-(4-bromobenzoyl)ethylene in 10 ml phosphorus trichloride was heated under reflux for 3–4 hr (TLC followed). The excess PCl$_3$ was removed by distillation and the residue was triturated with ice/water (exothermic reaction). The solution was extracted with dichloromethane (75 ml) and the dichloromethane layer was washed with saturated sodium bicarbonate solution, water, and dried (Na$_2$SO$_4$). The solvent was removed under reduced pressure. The residual solid was chromatographed over silica gel using ether:hexane (2:8 to 1:1) as eluant. An off white crystalline solid was obtained, 2.78 g (56%), mp 92°–3° C. IR (KBr) 2923, 2851, 1560, 1506, 1467, 1390, 1209, 1072, 1066, 945, 825, 707, 486. $^1$H NMR (CDCl$_3$/35° C.) 7.69 (d, 2H, J=8.8), 7.46–7.43 (m, 6H), 7.12 (d, 2H, J=8.3), 7.0 (d, 2H, J=8.3), 6.47 (s, 1H), 2.31 (s, 3H). $^{13}$C NMR (CDCl$_3$/135° C.) 150.8, 150.1, 142.8, 139.3, 133.0, 131.9, 131.7, 130.3, 129.1, 128.6, 125.1, 125.0, 121.8, 120.5, 117.1, 102.7, 20.6. MS m/e 484 (M$^+$).

2,5-bis(4-Cyanophenyl)-3-(4-tolyloxy) furan. A mixture of the dibromo compound prepared above (2.5 g, 0.0051 mole) and cuprous cyanide (1.81 g, 0.02 mole) in 8 ml dry N-methyl-2-pyrrolidone was heated at ca. 200° C. under a nitrogen atmosphere for 2.5 hr (TLC followed), cooled, and poured into 200 ml of water. The precipitated solid was filtered, resuspended in 100 ml of water and 100 ml of 10% NaCN was added and the mixture was stirred for 3–4 hr. The solid was filtered, washed with water and placed in a soxlate device using acetone for ca. 24 hr. The acetone extract was reduced in volume and passed through a short column of neutral aluminum, the eluate was evaporated and the resulting solid was recrystallized from CHCl$_3$:ether (2:8) to give a yellow crystalline solid 1.2 g (62%), mp 198°–9° C. IR (KBr) 3067, 2223, 1618, 1303, 1505, 1402, 1220, 1169, 1008, 926, 840, 820, 668, 546 cm$^{-1}$. $^1$H NMR (CDCl$_3$/35° C.) 7.98 (d, 2H, J=8.8), 7.75 (d, 2H, 8.3), 7.68 (d, 2H, J=8.8), 7.65 (d, 2J=8.8), 7.19 (d, 2H, J=8.3), 7.05 (d, 2H, J=8.3), 6.66 (s, 1H), 2.36 (s, 3H). $^{13}$C NMR (CDCl$_3$/35° C.) 154.3, 150.3, 145.8, 139.1, 134.0, 133.6, 133.3, 132.7, 132.6, 130.5, 124.2, 123.8, 119.0, 118.6, 117.8, 111.5, 110.0, 104.5, 20.7. Anal. Calcd. for C$_{25}$H$_{16}$N$_2$O$_2$: C, 79.76; H, 4.28; N, 7.44; Found: C, 79.68; H, 4.31; N, 7.39. MS m/e 376 (M$^+$).

2,5-bis[(4-(4,5-dihydro-1H-imidazol-2-yl)phenyl)]-3-(4-tolyloxy) furan. The bis-nitrile prepared above [1 g (0.0026 mole)] was placed in 20 ml absolute ethanol and 50 ml absolute dioxane which was saturated with dry HCl gas at 0° C. The mixture was allowed to stir at room temperature for 4 days. A thick yellow precipitate formed, 100 ml of dry ether was added and the solid was filtered, washed with 100 ml dry ether and dried in vacuo at 25° C. for 5 hr to yield 0.78 g (66%) imidate ester hydrochloride. The imidate ester was resuspended into 25 ml dry ethanol and heated at gentle reflux with 0.31 g (0.0053 mole) ethylenediamine for 12 hr. The excess ethanol was removed by distillation and the residue was treated with water, basified with 1M NaOH (stirring and cooling). The yellow precipiate was filtered, washed with water, dried and recrystallized from boiling ethanol to yield 0.6 g (74%), mp 156°–7° C. IR (KBr) 3218, 2927, 2862, 1609, 1506, 1398, 1218, 1105, 987, 848, 669 cm$^{-1}$. $^1$H NMR (DMSO-d$_6$/50° C.) 7.94–7.84 (m, 8H), 7.21 (d, 2H, J=8.3), 7.12 (s, 1H), 7.08 (d, 2H, J=8.79), 3.63 (s, 4H), 3.62 (s, 4H), 2.28 (s, 3H). $^{13}$C NMR (DMSO-d$_6$/50° C.) 163.0, 162.9, 154.3, 150.4, 142.8, 139.0, 132.4, 130.8, 130.4, 130.1, 129.7, 128.5, 127.5, 127.4, 123.2, 122.6, 116.5, 104.0, 49.3, 49.2, 19.9. MS m/e 462 (M$^+$).

The free base [0.5 g (0.001 mole)] in 10 ml ethanolic HCl was heated at reflux 3 hr and added to diluted 50 ml dry ether. The resulting yellow precipitate was filtered, washed with dry ether and dried in vacuo at 80° C. for 24 hr, 0.48 g (90%), mp>300° C. Anal. Calculated for C$_{29}$H$_{26}$N$_4$O$_2$. 2 HCl: C, 65.04; H, 5.27; N, 10.46. Found C, 64.83; H, 4.99; N. 10.22. IR (KBr) 3422, 3235, 2964, 2775, 1609, 1506, 1370, 1289, 1206, 848, 667 cm$^{-1}$. $^1$H NMR (DMSO-d$_6$/D$_2$O/TSP/60° C.) 7.98–7.86 (m, 8H), 7.19 (d, 2H, J=8.79), 7.09 (s, 1H), 7.03 (d, 2H, J=8.3), 3.88 (s, 4H), 3.76 (s, 4H), 2.24 (s, 3H). $^{13}$C NMR (DMSO-d$_6$/D$_2$O/TSP/60° C.) 165.3, 165.3, 154.7, 151.2, 145.7, 139.5, 134.3, 134.2, 135.1, 131.2, 129.6, 129.5, 124.8, 124.1, 123.3, 121.6, 117.7, 106.0, 45.8, 45.6, 20.7.

EXAMPLE 13

Preparation of 2,5-Bis[4-(2-tetrahydro-pyrimidinyl)phenyl]-3-(4-tolyoxy)furan

A stirred mixture of imidate ester (1.08 g, 0.002 mole) and freshly distilled 1,3-diaminopropane (0.43 g, 0.006 mole) in 30 ml absolute ethanol was gently heated under reflux (protected from moisture) for 12 hr. The excess ethanol was removed under reduced pressure and the residue titrated with 50 ml distilled water. The mixture was made basic with 1M NaOH (pH 10) while cooling and stirring the precipitated free base was filtered washed with water, dried and recrystallized from hot ethanol to yield 0.80 g (81.6%); mp 190°–191° C. IR (KBr): 3267, 2931, 2858, 1609, 1505, 1369, 1216, 846, 666 cm$^{-1}$. $^1$H NMR (DMSO-d$_6$/50° C.) 7.88–7.78 (m, 8H), 7.2 (d, 2H, J=8.8), 7.12 (s, 1H), 7.07 (d, 2H, J=8.8), 3.38 (t, 8H, J=5.1), 2.28 (s, 3H), 1.75 (tt, 4H, J=5.1): $^{13}$C NMR (DMSO-d$_6$/50° C.) 154.4, 153.8, 153.4, 150.5, 142.8, 139.0, 134.5, 132.9, 132.4, 130.6, 130.3, 130.3, 126.8, 126.7, 123.1, 122.5, 116.6, 104.1, 41.0, 40.8, 20.0, 19.8; MS m/e 490 (M+).

A suspension of 0.5 g (0.001 mole) of the free base in 5 ml absolute ethanol was treated with 10 ml ethanolic HCl and heated under gentle reflux for 2 hr. 50 ml of dry ether was added and the yellow precipitate thus obtained was filtered and washed with dry ether and dried in vacuo at 60° C. for 12 hr. The yield of yellow solid 0.46 g (82%). Mp>320° C. IR (KBr): 3423, 3117, 3002, 1638, 1609, 1507, 1375, 1315, 1202, 846, 669 cm$^{-1}$; $^1$H NMR (DMSO-d$_6$/D$_2$O/TSP/65° C.) 8.12 (d, 2H, J=7.8), 8.08 (d, 2H, J=7.3), 7.88 (d, 4H, J=8.3), 7.32 (d, 2H, J=8.3), 7.22 (s, 1H), 7.16 (d, 2H, J=8.3), 3.6 (br m, 8H), 2.37 (s, 3H), 2.1 (br m, 4H). $^{13}$C NMR (DMSO-d$_6$/D$_2$O/TSP/65° C): 159.5, 154.8, 151.1, 145.1, 140.9, 139.6, 134.1, 133.9, 133.5, 133.2, 128.7, 128.5, 127.2, 124.8, 117.6, 105.9, 41.5, 41.4, 20.6, 18.2. Anal. calculated for: C$_{31}$H$_{30}$N$_4$O$_2$.2HCl. C, 66.06; H, 5.36; N, 9.94. Found: C, 65.91; H, 5.21; N, 9.88.

EXAMPLE 14

Preparation of 2,5-Bis[4-(2-imidazolinyl)phenyl]-3-methoxyfuran 1,2-Bis(4-bromobenzoyl)-1-methoxyethane. To a solution of 1,2-dibromo-1,2-di(4-bromobenzoyl) ethane (11.1 g, 0.02 mole) in 150 ml dry methanol was added a solution of sodium methoxide in methanol (0.92 g sodium in 50 ml methanol). The yellow brown mixture was refluxed for 1–1.5 hr. The solvent was removed by distillation, the residue was suspended in water and the mixture was extracted with 100 ml chloroform. The chloroform extract was washed with water, dried (Na$_2$SO$_4$) and concentrated. The residue obtained was titrated with dry methanol-ether (3:1) to yield off-white crystalline solid, 6.6 g (78%), mp 153°–154° C. IR (KBr): 3106, 3062, 2932, 1689, 1649, 1583, 1556, 1403, 1223, 1202, 1182, 1086, 1010, 1000, 857, 814, 738, 618, 472 cm$^{-1}$. $^1$H (DMSO-d$_6$/40° C.): 7.95 (d, 2H, J=7.8), 7.77 (4H, J=8.8), 7.72 (d, 2H, J=7.8), 6.89 (s, 1H), 4.03 (s, 3H). $^{13}$C (DMSO-d$_6$/40° C.): 189.9, 187.2, 168.8, 139.9, 135.9, 133.1, 132.2, 131.8, 130.3, 128.1, 127.4, 98.6, 58.5. MS m/e 424 (M+).

2,5-Bis-[4-bromophenyl]-3-methoxy furan. The methoxyethane prepared above was dissolved in 5 ml PCl$_3$ and heated at reflux for 3 hr. The excess PCl$_3$ was removed by distillation. When treated with ice and water, the residue formed a gummy mass. The mixture was extracted with chloroform, and the organic layer was washed with water, dried (Na$_2$SO$_4$) and purified by column chromatography over silica gel using hexane: ether (4:1 to 2:1). An off-white solid in 62% yield was obtained; mp 112°–113° C. [lit. mp 113° C.; R. E. Lutz, *J. Am. Chem. Soc.* 51, 3008 (1929)]. IR (KBr): 3062, 2908, 2877, 1617, 490, 1391, 1211, 1160, 1099, 1073, 1034, 1006, 925, 827, 787. $^1$H NMR (CDC$_{13}$) 7.69 (d, 2H, J=8.8), 7.67.5 (m, 4H), 7.47 (d, 2H, J=8.8), 6.64 (s, 1H), 3.9 (s, 3H). $^{13}$C NMR (CDCl$_3$) 149.7, 147.5, 135.5, 131.9, 131.5, 129.4, 129.3, 125.0, 124.5, 121.5, 119.3, 98.6, 58.6. MS m/e 408 (M+).

2,5-Bis(4-cyanophenyl)-3-methoxy furan. A mixture of 2,5-bis(bromophenyl)-3-methoxyfuran (4.08 g, 0.01 mole) and cuprous cyanide (3.09 g, 0.035 mole) in 10 ml dry N-methyl-2-pyrrolidone was heated ca. 200° C. under N$_2$ for 2.5 hr. The mixture was cooled and poured into 200 ml of water and the precipitated yellow-brown solid was filtered and washed thoroughly with water. The solid was resuspended in water (50 ml) and 100 ml of 10% NaCN and stirred for 2 hr. The slurry was filtered, washed with water, dried and suspended in 250 ml of acetone and passed through a neutral alumina column. On elution with acetone a yellow solid resulted. On recrystallization from $CHCl_3$:ether (1:1) it gave (1.8 g, 60%) mp 257°–258° C. IR (KBr) 3128, 2223, 1608, 1599, 1501, 1409, 1174, 1163, 1027, 924, 836, 815, 651, 537 $cm^{-1}$. $^1H$ NMR (DMSO/45° C.) 8.03 (d, 2H, J=8.3), 7.95 (d, 2H, J=8.79), 7.91 (d, 2H, J=8.3), 7.85 (d, 2H, J=8.79), 7.62 (s, 1H), 4.0 (s, 3H). $^{13}C$ NMR (DMSO/45° C) 150.0, 149.8, 134.6, 133.4, 133.2, 132.7, 132.5, 124.0, 122.7, 118.9, 118.5, 110.0, 107.6, 102.4, 59.0. MS m/e 300 (M+). Anal. Calculated for: $C_{19}H_{12}N_2O$ (300.31): C, 75.98; H, 4.03; N, 9.33; Found: C, 76.02; H, 4.04; N, 9.36.

2,5-Bis[4-(2-imidazolinyl)phenyl]-3-methoxyfuran. The bis-nitrile prepared above (0.9 g, 0.003 mole) was suspended in 70 ml dry ethanol, saturated with dry HCl gas at 0°–5° C. and stirred under dry conditions for 3–4 days. The mixture was diluted with 200 ml dry ether and the yellow amidate ester was filtered and washed with dry ether and the solid was dried in vacuo for 5–6 hr to yield 1.2 g (86%). The solid was resuspended in 30 ml dry ethanol and refluxed gently with 0.46 g (0.008 mole) dry ethylenediamine for 12 hr. The solvent was removed by distillation. The residue was suspended with 50 ml cold water and made basic with 1M NaOH. The yellow precipitate was filtered, washed with water and dried. Recrystallization from ethanol-ether mixture yielded 0.74 g (75%) mp 186°–187° C. (dec.). IR (KBr) 3444, 3245, 2931, 2857, 1601, 1512, 1397, 1366, 1277, 1162, 1104, 1031, 926, 842, 743, 670 $cm^{-1}$. $^1H$ (DMSO-$d_6$/60° C.) 7.93–7.86 (m, 8H), 7.32 (s, 1H), 3.98 (s, 3H), 3.69 (s, 4H), 3.67 (s, 4H). $^{13}C$ NMR (DMSO-$d_6$/60° C.: 163.3, 163.1, 150.0, 148.6, 138.3, 134.7, 131.9, 131.3, 128.9, 127.6, 126.1, 123.0, 121.9, 100.6, 58.7, 49.0, 48.5. MS m/e 386 (M+).

The free base 0.58 g (0.0015 mole) was dissolved in 10 ml hot ethanol and treated with 10 ml sat. ethanolic HCl. The mixture was heated at reflux for 30 min. The volume was reduced under vacuum to 5–6 ml. The resulting mixture was diluted to 60 ml of dry ether. The yellow crystalline solid obtained was filtered, washed with dry ether and dried in vacuo at 60° C. for 12 to yield 0.62 g (83%), mp 189°–190° C. (dec.). IR (KBr): 3422, 3128, 2975, 1599, 1510, 1405, 1363, 1285, 1207, 1028, 845, 666 $cm^{-1}$. $^1H$ ($D_2O$/TSP/50° C.) 7.52–7.43 (m, 8H), 6.87 (s, 1H), 3.92 (s, 3H), 3.86 (s, 8H). $^{13}C$ ($D_2O$/TSP/50° C.) 167.2, 153.1, 152.4, 137.6, 137.6, 137.2, 130.9, 130.7, 126.5, 125.4, 122.1, 119.8, 104.2, 61.5, 47.0, 46.9. Anal. Calculated for: $C_{23}H_{22}N_4O_2$-0.5 $H_2O$-2HCl: C, 58.97; H, 5.38; N, 11.96. Found: C, 59.16; H, 5.35; N, 11.80.

EXAMPLE 15

Preparation of 2,5-Bis[4(N-cyclopropylguanyl)phenylfuran

A mixture of the imidate ester (1.3 g, 0.003 mole), cyclopropylamino (0.43 g, 0.0075 mole) in 35 ml of dry ethanol was stirred overnight. The solvent was removed in vacuo and water was added to make a yellow solution. The solution was made basic with 1M NaOH while cooling and stirring The solid which formed was filtered, washed with water and dried. The solid was dissolved in chloroform, dried over $Na_2SO_4$ and the solvent removed. The residue was recrystallized from ether:$CHCl_3$(5:1) to give a pale yellow solid 0.8 g (709%) mp 185°–186° C. (dec.). IR (KBr): 3464, 3320, 3080, 1610, 1510, 1364, 1022, 848, 791 $cm^{-1}$. $^1H$ NMR ($CDCl_3$): 7.71 (br s, 8H), 6.78 (s, 2H), 5.3 (v br, 4H), 2.6 (br m, 2H), 0.87–0.81 (m, 4H), 0.67–0.62 (m, 4H). $^{13}C$ NRM ($CDCl_3$+DMSO-$d_6$): 159.6, 152.2, 134.8, 130.7, 126.4, 122.6, 107.7, 25.7, 6.04. MS m/e 388 (M+).

The free base (0.6 g, 0.0015 mole) was suspended in 3 ml of dry ethanol and was treated with 6 ml ethanolic HCl and heated gently at 65° C. for 1 hr. The yellow solution was diluted with 50 ml dry ether and filtered, washed with dry ether and dried in vacuo at 75° C. for 12 hr. The yield of yellow solid was 0.55 g (80%), mp>310° C. (dec.). IR (KBr): 3369, 3181, 3037, 1665, 1607, 1502, 1032, 782, 674 $cm^{-1}$. $^1H$ NMR (DMSO-$d_6$): 10.24 (s, 2H), 9.86 (s, 2H), 9.27 (s, 2H), 8.06 (d, 4H, J=7.94), 7.95 (d, 4H, J=8.54), 7.42 (s, 2H), 2.87 (br m, 2H), 1.09–0.85 (m, 8H). $^{13}C$ NMR (DMSO-$d_6$): 163.9, 152.3, 133.7, 129.1, 126.6, 123.5, 111.3, 24.7, 6.5. Anal. Calculated for: $C_{24}H_{24}N_4O$-2HCl: Cal. C, 63.02; H, 5.73; N, 12.25. Found: C, 62.89; H, 5.95; N, 12.00.

EXAMPLE 16

In Examples 16–19, results are presented for a series of compounds. The following compound designations are used throughout.

| Compound | Name |
| --- | --- |
| 1 | 2,5-bis(4-guanylphenyl)furan |
| 2 | 2,5-bis[4-(2-imidazolinyl)phenyl]furan |
| 3 | 2,5-di-p[2(3,4,5,6-tetrahydropyrimidiyl)phenyl]furan |
| 4 | 2,5-bis[4-(4,5,6,7-tetrahydro-1H-1,3-diazepin-2-yl)phenyl]furan |
| 5 | 2,5-bis[4-(3a,4,5,6,7,7a-hexahydro-1H-benzimidazol-2-yl)phenyl]furan |
| 6 | 2,5-bis{4[2-(N-2-hydroxyethyl)imidazolinyl]-phenyl}furan |
| 7 | 2,5-bis-{4-[2-(N-ethylimidazolinyl)phenyl}furan |
| 8 | 2,5-bis(4-guanylphenyl)-3,4-dimethyl furan |
| 9 | 2,5-[bis{4-(2-imidazolinyl)}phenyl]3-p-tolyloxy furan |
| 10 | 2,5-[bis{4-(2-tetrahydropyrimidinyl)}phenyl]3]p]tolyloxy furan |
| 11 | 2,5-bits{4-[5-(N-2-aminoethylamido)benzimidazol-2-yl]phenyl}furan |
| 12 | 2,5-bis(4-N,N-dimethylcarboxyhydrazidephenyl)furan |
| 13 | 2,5-bis[4-(N-isopropylamidino)phenyl]furan |
| 14 | 2,5-bis{4-[3-(dimethylaminopropyl)amindino]phenyl}furan, |
| 15 | 2,5-bis-[4-N-(cyclopropylguanyl)phenyl]furan |
| 16 | 2,5-bis-{4-[(N-2-hydroxyethyl)guanyl]phenyl}furan |
| 17 | 2,5-bis[4-N-(dimethylaminoethyl)guanyl]phenyl furan |
| 18 | 2,5-bis[2-(imidzaolinyl)phenyl]-3,4-bis(methoxymethyl)furan |
| 19 | 2,5-bis-{4-[N-(3-aminopropyl)amindino]phenyl}furan |
| 20 | 2,5-bis[4-(N-isopropylamidino)phenyl]-3-methyl furan, |

DNA THERMAL MELTING

Thermal melting curves for DNA and its complexes with compounds from Examples 4, 6, and 7–9 are determined as previously described in F. A. Tanious, et al., *J. Biomol. Structure & Dynamics* 11:1063 (1994) and W. D. Wilson, et al., *Biochemistry* 32:4098 (1993), by following the adsorption change at 260 nm as a function of temperature. Tm values were determined from first derivative plots. Compounds are compared by the increase in Tm (Δ, Tm=Tm of complex—Tm of the free nucleic acid) they produce in MES buffer (0.01M 2-(N-morpholino) ethanesulfonic acid, 0.001M EDTA, 0.1M NaCl adjusted to pH 6.0) at saturating amounts of compound (a ratio of 0.3 moles of compound to nucleic acid bases) unless otherwise indicated.

TABLE 1

Nucleic Acid Binding Results for Dicationic Diarylfurans

| Compound | ΔTm DNA[1] | ΔTm Oligomer[2] |
|---|---|---|
| 1 | 25 | 11.7 |
| 2 | 24 | 11.4 |
| 3 | >28 | 13.5 |
| 4 | >28 | 10.7 |
| 5 | 24.5 | 5.6 |
| 6 | 12.2 | 1.0 |
| 7 | 11.8 | — |
| 9 | 18.1 | — |
| 10 | >28 | — |
| 11 | −26 | — |
| 13 | 23.1 | — |
| 14 | >28 | — |
| 15 | >28 | — |
| 16 | 21.1 | — |

[1] Increase in thermal melting of polyA · polyT. See, W. D. Wilson, et al., Biochemistry 32:4098 (1993).
[2] Increase in thermal melting of the oligomer d(GCGCAATTGCGC)$_2$. See, F. A. Tanious, et al., J. Biomol. Structure & Dynamics 11:1063 (1994).

EXAMPLE 17

Topoisomerase II Inhibition and *Giardia lamblia* Inhibition by Dicationic Diarylfurans

TABLE 2

Topoisomerase II inhibition and Anti-*Giardia lamblia*

| | IC$_{50}$(μM) | | | |
|---|---|---|---|---|
| | Topoisomerase Activity | | | *Giardia* |
| Compound | G.l.[1] | D.m.[2] | I[3] | *lamblia*[4] |
| 1 | 0.5–1 | 2.0 | 100 | 0.2 |
| 2 | 3–5 | 8 | 50–100 | 0.8 |
| 3 | 0.5–1 | 2.5 | >100 | 0.06 |
| 4 | 1.5 | 25–50 | — | 1.1 |
| 5 | 3–6 | 50 | — | 1.7 |
| 6 | 20 | 200 | — | 5.3 |
| 7 | 25 | — | — | — |
| 8 | 0.75 | 2.4 | <3.12 | 0.26 |
| 9 | 2–4 | 25 | 12.5 | >100 |
| 10 | 1–3 | 50–100 | — | 3.3 |
| 11 | 5.0 | >300 | — | 0.62 |
| 12 | 0.6–1.2 | 30–60 | — | 0.35 |
| 13 | 0.5–1 | 15–30 | — | 0.14 |
| 14 | 0.25 | >6.2 | — | 8.98 |
| 15 | 1.25 | — | — | 0.63 |
| 16 | 1.2–2.5 | 25–50 | — | 0.78 |
| 17 | 0.8 | 12.5 | — | 10.78 |
| 18 | 0.8–1 | 12.5 | — | 4.42 |
| 19 | 0.625 | 25 | — | 0.059 |
| 20 | 1–2 | 3 | 50–100 | 4.4 |

[1] 50% inhibition of topoisomerase II isolated from *Giardia lamblia*. See, C. A. Bell, et al., Antimicrob. Agents and Chemother. 37:2668 (1993).
[2] 50% inhibition of topoisomerase II isolated from *Drosophila melanogaster*.
[3] 50% inhibition of topoisomerase I isolated from *Pneumocystis carinii*.
[4] 50% inhibition of growth of *Giardia lamblia* in in vitro culture. See, C. A. Bell, al., supra.

EXAMPLE 18

Activity Against *Pneumocystis Carinii* pneumonia

TABLE 3

In vivo Activity of Dicationic Diaryl Furans Against *Pneumocystis carinii*

| Compound | Dosage[1] (μM/kg/day) | Toxicity[2] | cyst/g lung[3] (% of control) |
|---|---|---|---|
| Saline | | | 100 |
| Pentamidine | 22.1 | +2 | 3.66 |
| 1 | 13.3 | 0 | 2.1 |
| | 2.7 | 0 | 8.3 |
| | 0.27 | 0 | 4.8 |
| | 0.027 | 0 | 55.9 |
| | 66.3[4] | 0 | 28.4 |
| 2 | 23.3 | +2 | 35.4 |
| 3 | 10.9 | +2 | 0.4 |
| 4 | 2.3 | +3 | 2.9 |
| | 0.18 | 0 | 115.4 |
| 5 | 9.2 | +1 | 80.5 |
| 6 | 4.8 | +3 | 107.3 |
| 8 | 24.7 | +1 | 0.8 |
| 9 | 9.3 | +2 | 139.5 |
| 10 | 1.8 | +3 | 139.5 |
| 11 | 4.1 | +4 | 27.4 |
| 12 | 7.78 | +3 | 20.7 |
| 13 | 10.8 | 0 | 0.2 |
| 14 | 3.9 | +3 | 107.3 |
| 16 | 10.4 | 0 | 0.6 |

[1] Dosage intravenous except as noted.
[2] A detailed explanation of the toxicity scale is described in R. R. Tidwell, et al., Antimicrob. Agents and Chemother. 37:1713 (1993). Generally the larger the value the more severe the toxicity. Values greater than 2 indicate deaths of some animals.
[3] Counted cysts in a blinded protocol in lung tissue reported as percentage of saline-treated controls. See, R. R. Tidwell, et al., supra.
[4] Oral dosage by gavage.

EXAMPLE 19

Activity Against *Cryptosporidium parvum*

TABLE 4

**Activity of Dicationic Diaryl Furans Against *Cryptosporidium parvum***

| Compound | No. of mice[1] | Oocysts[2] | Std Error[3] | % Reduction | Score[4] | Prob.[5] |
|---|---|---|---|---|---|---|
| control | 28 | 36.71 | 2.99 | — | — | — |
| 1 | 21 | 6.6 | 1.9 | 66 | 2.96 | .0015 |
| 13 | 23 | 2.13 | 0.37 | 94.2 | 6.07 | <.0001 |

[1] Suckling ICR outbred Swiss mice. See, Blagburn et al., Antimicrobial Agents and Chemotherapy 35:1520 (1991).
[2] Mean oocyst count.
[3] Standard error of the mean.
[4] Mann-Whitney Z Score.
[5] Probability.

EXAMPLE 20

Preparation of 2,5-Bis[4-(N-2-methoxyethylguanyl)phenyl]furan

To a stirred suspension of 0.87 g (0.002 mole) of the furan bis-imidate ester hydrochloride in 15 ml absolute ethanol is added 0.45 g (0.006 mole) freshly distilled 2-methoxyethylamine. The mixture is stirred for 12 hours, the solvent is distilled under vacuum, ice-water is added, and the mixture is basified with 1M NaOH to pH 10. An oily paste separates from the water, it is washed with water, dissolved in $CHCl_3$ and dried over anhydrous sodium sulfate. The solvent is removed under vacuum, and the solid obtained is recrystallized from ether:chloroform (8:1) to give a solid 0.58 g (69%) having a mp of 118°–120° C. IR (KBr): 3430, 3370, 2887, 1647, 1603, 1547, 1367, 1192, 1110, 1021, 847, 787, 681 cm$^{-1}$. $^1$H NMR (CDCl$_3$) δ 7.75 (d, 4H, J=8.5), 7.63 (d, 4H, J=8.5), 6.8 (s, 2H), 3.68–3.61 (m, 4H), 3.60–3.75 (m, 4H), 3.41 (s, 3H). $^{13}$C NMR (CDCl$_3$) δ 136.2, 153.0, 136.5, 131.9, 126.6, 123.8, 100.5, 71.4, 58.8, 58.7. MS: m/e420(M+).

The freebase (0.42 g, 0.001 mole) is dissolved in 4 ml ethanolic HCl and stirred at 40°–45° C. for 2 hours, the solvent is removed under vacuum and the solid obtained is triturated with dry ether. The solid is filtered, washed with ether and dried in vacuum at 60° C. for 12 hours. The yield is 0.44 g (89%) of yellow solid having a mp of 208°–210° C. dec. IR (KBr): 3410, 3320, 3095, 1674, 1615, 1503, 1291, 1197, 1112, 788 cm$^{-1}$. $^1$H NMR (DMSO-d$_6$) δ 10.0 (brs, 2H), 9.65 (brs, 2H), 9.24 (brs, 2H), 8.09 (d, 4H, J=8.3), 7.91 (d, 4H, J=8.7), 7.42 (s, 2H), 3.7–3.62 (m, 8H), 3.33 (s, 6H). $^{13}$C NMR (DMSO-d$_6$) δ 162.4, 152.4, 133.8, 129.1, 127.3, 123.6, 111.4, 69.0, 58.2, 42.6. Analysis calculated for $C_{24}H_{28}N_4O_3 \cdot 2HCl \cdot 1.5H_2O$; theory C:55.38, H:6.39, N:10.76; found: C:55.23, H:6.41, N:10.61.

EXAMPLE 21

Preparation of 2,5-Bis[4{N-(3-pentylguanyl)phenyl}]furan

Freshly distilled 3-aminopentane (0.34 g, 0.004 mole) is added to a stirred suspension of the furan bis-imidate ester (0.65 g, 0.0015 mole) in 10 ml absolute ethanol, after 5 min. the reaction mixture became clear. This mixture is stirred for 12 hours, and the solvent is removed under vacuum. The residue is treated with 10 ml ice-cold water, and basified to pH 10 with 1M NaOH. The off-white precipitate is filtered, washed with water, dried and recrystallized from CHCl$_3$:ether (1:3) to give 0.51 g (76%) pale solid, having a mp of 155°–156° C. IR (KBr): 3245, 3120, 2962, 1593, 1544, 1380, 1194; 848, 784 cm$^{-1}$. $^1$H NMR (DMSO-d$_6$) δ 157.3, 152.5, 136.7, 130.5, 127.0, 122.8, 108.8, 55.0, 27.3, 10.5. MS: m/e444(M+).

The freebase (0.35 g, 0.00078 mole) is dissolved in 5 ml of warm dry ethanol. Ethanolic HCl (5 ml) is added, and the solution is allowed to stir at room temperature for 4 hours. The solvent is removed under vacuum and the oil obtained is triturated with dry ether. A yellow solid is collected by filtration, washed with ether and dried at 75° C. for 12 hours under vacuum. The yield is 0.36 g (90%) of product having a top>360°. IR (KBr): 3410, 3235, 3105, 1668, 1613, 1500, 1459, 1368, 1126, 1025 cm$^{-1}$. $^1$H NMR (D$_2$O/DMSO-d$_6$/45° C.) δ 7.93 (d, 4H, J=8.5), 7.76 (d, 4H, J=8.5), 7.13 (s,2H), 3.88–3.65 (m, 2H), 1.9–1.8 (m, 4H), 1.78–1.66 (m, 4H), 1.05 (t, 6H, J=7.3). $^{13}$C NMR(D$_2$O/DMSO-d$_6$/45° C.) δ 165.1, 154.1, 136.2, 130.0, 129.0, 125.8, 112.9, 59.1, 27.8, 11.5. Analysis calculated for $C_{28}H_{36}N_4O \cdot 2HCl \cdot 1.5H2O$; theory: C:58.32, H:7.16, N:9.71; found: C:58.26, H:7.31, N:9.63.

EXAMPLE 22

Preparation of 2,5-Bis[4-cyanophenyl]furan

To a suspension of NaH (2.5 g, 0.11 mole) in 50 ml dry THF under nitrogen is added a solution of diethyl carbonate (11.8 g, 0. I mole) in 20 ml dry THF. After stirring for 5 min. 4'-bromoacetophenone (19/9 g, 0.1 mole) in 50–60 ml dry THF is added dropwise over 3–4 hours. The yellow reaction mixture is stirred overnight, the solvent is removed under vacuum, and the remaining oil is diluted with water. The mixture is then extracted with 2×100 ml portions of ether. The ether is dried over anhydrous sodium sulfate, and removed to yield a pale oil. The oil is purified by column chromatography over silica gel (elution: hexane-5:1 hexane:ether) or distilled under high vacuum (pressure 0.01 mm) to yield a pale oil 18.8 g (70%). Product is stored at 0° C. and used immediately.

Ethyl 3-[4-Bromophenyl]-3-oxopropionate (13.5 g, 0.05 mole), obtained above, in 20 ml dry EtOH is added to a solution of sodium ethoxide (1.15 g Na, 0.05 mole in 30 ml ethanol) under nitrogen. The solution is stirred for 30 min., cooled and 4-bromophenacyl bromide (13.85 g, 0.05 mole) in 75 ml dry EtOH is added slowly over a period of 30–40 min. The mixture is allowed to stir at room temperature for 3 days. The solvent is removed in vacuum, the oil is diluted with water, extracted with ether, washed with water and dried over magnesium sulfate. The solution is filtered and the solvent removed to yield crude oil 16.0 g (68%). Any remaining solvent is removed by placing in vacuum for 2 hours at room temperature.

The crude oil (0.034 mole), ethyl 2,3-bis[4-bromobenzoyl]propionate, is dissolved in 75–80 ml dry EtOH, saturated with dry HCl at 0° C., and allowed to stir at room temperature for 24 hours. The resulting solid is filtered, washed with cold ethanol, and then suspended in water and extracted with $CH_2Cl_2$. The organic layer is dried over magnesium sulfate and the solvent removed to yield 7.4 g (48%) of the furan ester as a white crystalline solid having a mp of 125°–127° C. $^1$H NMR(CDCL$_3$) δ 7.97 (d, 2H, J=8.8), 7.58 (d, 2H, J=8.8), 7.56–7.52 (m, 4H), 7.07 (s, 1H), 4.3 (q, 2H, J=8.8), 1.38 (t, 3H, J=8.8). $^{13}$C NMR (CDCl$_3$) δ 163.2, 155.5, 151.5, 132.1, 131.5, 139.8, 128.5, 128.4, 125.5, 123.9, 122.2, 116.4, 108.7, 60.9, 14.3.

This ester (7.0 g, 0.015 mole) is suspended in 75 ml 20% KOH and 10 ml EtOH, and heated under reflux for 4–5 hours. After cooling and acidification with concentrated HCl the solid precipitate is filtered, washed with water, dried in air and in vacuum to yield 5.4 g (82%) of the acid having a mp of 252°–254° C. $^1$NMR (CDCl$_3$) δ 8.03 (d, 2H, J=8.8), 7.77 (d, 2H, J=8.4), 7.67 (d, 2H, J=8.8), 7.62 (d, 2H, J-8.4), 7.37 (s, 1H), 3.4 (br, 1H). $^{13}$C NMR (CDCl$_3$) δ 163.8, 153.9, 150.8, 131.7, 131.1, 129.6, 128.2, 128.1, 125.7, 122.7, 121.2, 117.2, 109.6.

A mixture of 2,5-bis(4-bromophenyl)-3-furan carboxylic acid 0.85 g (0.002 mole), CuCN 0.45 g (0.005 mole) in 10 ml freshly distilled quinoline is heated under reflux for 3 hours. The mixture is cooled and 100 ml dilute aqueous HCl is added and the mixture is stirred for 30 min. and filtered. The solid is washed with water and then with hexane. The resultant yellow solid is dissolved in acetone and passed through an alumina (neutral) column to yield a yellow crystalline solid 0.37 g (68%) having amp of 293°–295° C. The product is identical with that described in Example 1.

EXAMPLE 23

Preparation of 2,5-Bis-(N-isopropylguanyl)phenyl]-3-methylfuran

To a suspension of imidate ester dihydrochloride (0.45 g, 0.001 mole) in 10 ml of dry ethanol is added distilled isopropyl amine (0.18 g, 0.003 mole) and the mixture is stirred for 12 hours. The solvent is removed under vacuum and the residue is stirred with 10 ml ice/water, basified with 1M NaOH and the pH is adjusted to 10. The solid obtained is filtered, dried and crystallized from ether:CHCl$_3$ (3:1) to yield 0.31 g (77%) yellow gummy solid. MS: m/e 402(M$^+$).

The freebase (0.20 g, 0.0005 mole) is dissolved in 5 ml ethanol and stirred with 5 ml ethanolic HCl for 2 hours. The ethanol is distilled under vacuum and the residue is triturated with dry ether to yield 0.29 g of yellow solid (73%) having a mp of 260°–262° C. IR(KBr): 3377, 3210, 3050, 1668, 1611, 1508, 1391, 1128, 932, 842 cm$^{-1}$. $^1$H NMR(D$_2$O/DMSOd$_6$) δ 9.65 (br, 2H), 9.55 (br, 2H), 9.7 (br, 2H), 8.0 (d, 2h, J=8.8), 7.94 (d, 2H, J=8.79), 7.91 (d, 2H, J=8.3), 7.84 (d, 2H, J=8.3), 7.29 (s, 1H), 4.10 (brm, 2H), 2.38 (s, 3H), 1.27 (bd, 12H). $^{13}$C NMR(D$_2$O/DMSOd$_6$/65° C.) δ 163.1, 163.0, 151.6, 148.2, 136.6, 135.5, 129.3, 129.1, 127.7, 126.9, 125.9, 125.1, 124.3, 115.9, 47.1, 21.9, 13.2. Analysis calculated for $C_{25}H_{30}N_4O.2HCl.H_2O$:theory: C:60.84, H:6.94, N: 11.35; found C:60.79, H:7.01, N:11.27.

The foregoing is illustrative of the present invention and is not to be construed as limiting thereof. The invention is defined by the following claims, with equivalents of the claims to be included therein.

That which is claimed is:

1. A method of treating *Pneumocystis carinii* pneumonia in a subject in need of such treatment, comprising administering to said subject a compound of Formula (I):

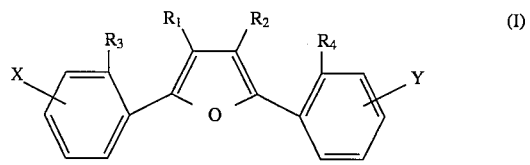

wherein:

$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;

$R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

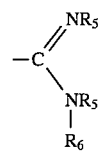

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof, in an amount effective to treat *Pneumocystis carinii* pneumonia.

2. The method according to claim 1, wherein said subject is afflicted with *Pneumocystis carinii* pneumonia.

3. The method according to claim 1, wherein said subject is at risk of developing *Pneumocystis carinii* pneumonia, said treatment is a prophylactic treatment, and said compound is administered in a prophylactically effective amount.

4. The method according to claim 1, wherein X and Y are in the para position.

5. The method according to claim 1, wherein X and Y are each

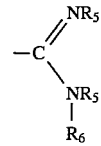

and wherein said compound of Formula (I) is selected from the group consisting of compounds wherein (a) each $R_1$ is H, $R_2$ is H, $R_3$ is H, $R_4$ is H, $R_5$ is H, and $R_6$ is H;

(b) $R_1$ is H, $R_2$ is H, $R_3$ is H, $R_4$ is H, two $R_5$ groups together represent $C_2$ alkyl, and $R_6$ is H;

(c) $R_1$ is H, $R_2$ is H, $R_3$ is H, $R_4$ is H, two $R_5$ groups together represent $C_3$ alkyl, and $R_6$ is H;

(d) $R_1$ is loweralkyl, $R_2$ is loweralkyl, $R_3$ is H, $R_4$ is H, $R_5$ is H, and $R_6$ is H;

(e) $R_1$ is oxyalkyl, $R_2$ is oxyalkyl, $R_3$ is H, $R_4$ is H, two $R_5$ groups together represent $C_2$ alkyl, and $R_6$ is H;

(f) $R_1$ is H, $R_2$ is oxyalkyl, $R_3$ is H, $R_4$ is H, two $R_5$ groups together represent $C_2$ alkyl, and $R_6$ is H;

(g) $R_1$ is H, $R_2$ is oxyarylalkyl, $R_3$ is H, $R_4$ is H, two $R_5$ groups together represent $C_2$ alkyl, and $R_6$ is H;

(h) $R_1$ is H, $R_2$ is H, $R_3$ is H, $R_4$ is H, two $R_5$ groups together represent $C_2$ alkyl, and $R_6$ is hydroxyalkyl;

(i) $R_1$ is H, $R_2$ is oxyarylalkyl, $R_3$ is H, $R_4$ is H, two $R_5$ groups together represent $C_3$ alkyl, and $R_6$ is H;

(j) $R_1$ is H, $R_2$ is H, $R_3$ is H, $R_4$ is H, $R_5$ is H, and $R_6$ is aminoalkyl;

(k) $R_1$ is H, $R_2$ is H, $R_3$ is H, $R_4$ is H, two groups $R_5$ groups together represent $C_4$ alkyl, and $R_6$ is H;

(i) $R_1$ is H, $R_2$ is H, $R_3$ is H, $R_4$ is H, $R_5$ is H, and $R_6$ is alkyl;

(m) $R_1$ is H, $R_2$ is H, $R_3$ is H, $R_4$ is H, $R_5$ is H, and $R_6$ is alkylamino;

(n) $R_1$ is H, $R_2$ is H, $R_3$ is H, $R_4$ is H, $R_5$ is H, and $R_6$ is hydroxyalkyl;

(o) $R_1$ is H, $R_2$ is H, $R_3$ is H, $R_4$ is H, $R_5$ is H, and $R_6$ is alkylaminoalkyl;

(p) $R_1$ is H, $R_2$ is loweralkyl, $R_3$ is H, $R_4$ is H, $R_5$ is H, and $R_6$ is loweralkyl; and (q) $R_1$ is H, $R_2$ is H, $R_3$ is H, $R_4$ is H, two $R_5$ groups together represent $C_2$ alkyl, and $R_6$ is loweralkyl.

6. The method according to claim 1, wherein said compound of Formula (I) is selected from the group consisting of 2,5-bis(4-guanylphenyl)furan, 2,5-bis(4-guanylphenyl)-3,4-dimethylfuran, 2,5-di-p[2(3,4,5,6-tetrahydropyrimidyl)phenyl]furan, 2,5-bis[4-(2-imidazolinyl)phenyl]furan, 2,5-[bis-{4-(2-tetrahydropyrimidinyl)}phenyl]3-p(tolyloxy)furan, 2,5-[bis{4-(2-imidazolinyl)}phenyl]3-p(tolyloxy) furan, 2,5-bis{4[2-(N-2-hydroxyethyl)imidazolinyl]-phenyl}furan, 2,5-bis[4-(N-isopropylamidino)phenyl]furan, 2,5-bis{4-[3-(dimethylaminopropyl)amidino]phenyl}furan, 2,5-bis-{4-[N-(3-aminopropyl)amidino]phenyl}furan, 2,5-bis[2-(imidzaolinyl)phenyl]-3,4-bis(methoxymethyl)-furan, 2,5-bis[4-N-(dimethylaminoethyl)guanyl]phenyl furan, 2,5-bis-{4-[(N-2-hydroxyethyl)guanyl]phenyl}furan, 2,5-bis-[4-N-(cyclopropylguanyl)phenyl]furan, 2,5-bis[4-(N,N-diethylaminopropyl)guanyl]phenyl furan, 2,5-bis-{4-[2-(N-ethylimidazolinyl)]phenyl}furan, 2,5-bis-{4-[N-(3-pentylguanyl)amindino]}phenylfuran, 2,5-bis-[4-(2-imidazolinyl)phenyl]-3-methoxyfuran, 2,5-bis[4-(N-isopropylamidino)phenyl]-3-methylfuran, and the pharmaceutically acceptable salts thereof.

7. A method of treating *Giardia lamblia* in a subject in need of such treatment, comprising administering to said subject a compound of Formula (I):

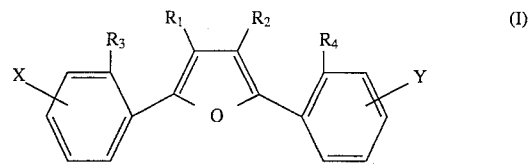

wherein:

$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;

$R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

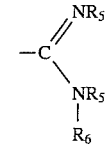

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a phamaceutically acceptable salt thereof, in an amount effective to treat *Giardia lamblia*.

8. The method according to claim 7, wherein said subject is afflicted with *Giardia lamblia*.

9. The method according to claim 7, wherein said subject is at risk of developing *Giardia lamblia*, said treatment is a prophylactic treatment, and said compound is administered in a prophylactically effective amount.

10. The method according to claim 7, wherein X and Y are in the para position.

11. The method according to claim 7, wherein X and Y are each

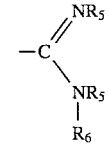

and wherein said compound of Formula (I) is selected from the group consisting of compounds wherein (a) each $R_1$ is H, $R_2$ is H, $R_3$ is H, $R_4$ is H, $R_5$ is H, and $R_6$ is H;

(b) $R_1$ is H, $R_2$ is H, $R_3$ is H, $R_4$ is H, two $R_5$ groups together represent $C_2$ alkyl, and $R_6$ is H;

(c) $R_1$ is H, $R_2$ is H, $R_3$ is H, $R_4$ is H, two $R_5$ groups together represent $C_3$ alkyl, and $R_6$ is H;

(d) $R_1$ is loweralkyl, $R_2$ is loweralkyl, $R_3$ is H, $R_4$ is H, $R_5$ is H, and $R_6$ is H;

(e) $R_1$ is oxyalkyl, $R_2$ is oxyalkyl, $R_3$ is H, $R_4$ is H, two $R_5$ groups together represent $C_2$ alkyl, and $R_6$ is H;

(f) $R_1$ is H, $R_2$ is oxyalkyl, $R_3$ is H, $R_4$ is H, two $R_5$ groups together represent $C_2$ alkyl, and $R_6$ is H;

(g) $R_1$ is H, $R_2$ is oxyarylalkyl, $R_3$ is H, $R_4$ is H, two $R_5$ groups together represent $C_2$ alkyl, and $R_6$ is H;

(h) $R_1$ is H, $R_2$ is H, $R_3$ is H, $R_4$ is H, two $R_5$ groups together represent $C_2$ alkyl, and $R_6$ is hydroxyalkyl;

(i) $R_1$ is H, $R_2$ is oxyarylalkyl, $R_3$ is H, $R_4$ is H, two $R_5$ groups together represent $C_3$ alkyl, and $R_6$ is H;

(j) $R_1$ is H, $R_2$ is H, $R_3$ is H, $R_4$ is H, $R_5$ is H, and $R_6$ is aminoalkyl;

(k) $R_1$ is H, $R_2$ is H, $R_3$ is H, $R_4$ is H, two groups $R_5$ groups together represent $C_4$ alkyl, and $R_6$ is H;

(l) $R_1$ is H, $R_2$ is H, $R_3$ is H, $R_4$ is H, $R_5$ is H, and $R_6$ is alkyl;

(m) $R_1$ is H, $R_2$ is H, $R_3$ is H, $R_4$ is H, $R_5$ is H, and $R_6$ is alkylamino;

(n) $R_1$ is H, $R_2$ is H, $R_3$ is H, $R_4$ is H, $R_5$ is H, and $R_6$ is hydroxyalkyl;

(o) $R_1$ is H, $R_2$ is H, $R_3$ is H, $R_4$ is H, $R_5$ is H, and $R_6$ is alkylaminoalkyl;

(p) $R_1$ is H, $R_2$ is loweralkyl, $R_3$ is H, $R_4$ is H, $R_5$ is H, and $R_6$ is loweralkyl; and (q) $R_1$ is H, $R_2$ is H, $R_3$ is H, $R_4$ is H, two $R_5$ groups together represent $C_2$ alkyl, and $R_6$ is loweralkyl.

12. The method according to claim 7, wherein said compound of Formula (I) is selected from the group consisting of 2,5-bis(4-guanylphenyl)furan, 2,5-bis(4-guanylphenyl)-3,4-dimethylfuran, 2,5-di-p[2(3,4,5,6-tetrahydropyrimidyl)phenyl]furan, 2,5-bis[4-(2-imidazolinyl)phenyl]furan, 2,5-[bis{4-(2-tetrahydropyrimidinyl)}phenyl]3-p(tolyloxy)furan, 2,5-[bis{4-(2-imidazolinyl)}phenyl]3-p(tolyloxy)furan, 2,5-bis{4-[2-(N-2-hydroxyethyl)imidazolinyl]-phenyl}furan, 2,5-bis[4-(N-isopropylamidino)phenyl]furan, 2,5-bis{4-[3-(dimethylaminopropyl)amidino]phenyl}furan, 2,5-bis-{4-[N-(3-aminopropyl)amidino]phenyl}furan, 2,5-bis[2-(imidzaolinyl)phenyl]-3,4-bis(methoxymethyl)-furan, 2,5-bis[4-N-(dimethylaminoethyl)guanyl]phenyl furan, 2,5-bis-{4-[(N-2-hydroxyethyl)guanyl]phenyl}furan, 2,5-bis-[4-N-(cyclopropylguanyl)phenyl]furan, 2,5-bis-[4-(N,N-diethylaminopropyl)guanyl]phenyl furan, 2,5-bis-{4-[2-(N-ethylimidazolinyl)]phenyl}furan, 2,5-bis-{4-[N-(3-pentylguanyl)amindino]}phenylfuran, 2,5-bis-[4-(2-imidazolinyl)phenyl]-3-methoxyfuran, 2,5-bis[4-(N-isopropylamidino)phenyl]-3-methylfuran, and the pharmaceutically acceptable salts thereof.

13. A method of treating *Cryptosporidium parvum* in a subject in need of such treatment, comprising administering to said subject a compound of Formula (I):

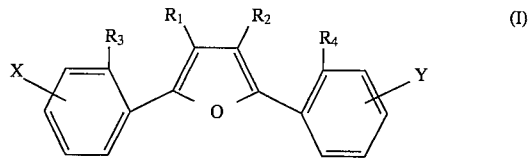

wherein:

$R_1$ and $R_2$ are each independently selected from the group consisting of H, loweralkyl, aryl, alkylaryl, aminoalkyl, aminoaryl, halogen, oxyalkyl, oxyaryl, or oxyarylalkyl;

$R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

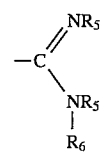

wherein:

each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof, in an amount effective to treat *Cryptosporidium parvum*.

14.

(f) $R_1$ is H, $R_2$ is oxyalkyl, $R_3$ is H, $R_4$ is H, two $R_5$ groups together represent $C_2$ alkyl, and $R_6$ is H;

(g) $R_1$ is H, $R_2$ is oxyarylalkyl, $R_3$ is H, $R_4$ is H, two $R_5$ groups together represent $C_2$ alkyl, and $R_6$ is H;

(h) $R_1$ is H, $R_2$ is H, $R_3$ is H, $R_4$ is H, two $R_5$ groups together represent $C_2$ alkyl, and $R_6$ is hydroxyalkyl;

(i) $R_1$ is H, $R_2$ is oxyarylalkyl, $R_3$ is H, $R_4$ is H, two $R_5$ groups together represent $C_3$ alkyl, and $R_6$ is H;

(j) $R_1$ is H, $R_2$ is H, $R_3$ is H, $R_4$ is H, $R_5$ is H, and $R_6$ is aminoalkyl;

(k) $R_1$ is H, $R_2$ is H, $R_3$ is H, $R_4$ is H, two groups $R_5$ groups together represent $C_4$ alkyl, and $R_6$ is H;

(l) $R_1$ is H, $R_2$ is H, $R_3$ is H, $R_4$ is H, $R_5$ is H, and $R_6$ is alkyl;

(m) $R_1$ is H, $R_2$ is H, $R_3$ is H, $R_4$ is H, $R_5$ is H, and $R_6$ is alkylamino;

(n) $R_1$ is H, $R_2$ is H, $R_3$ is H, $R_4$ is H, $R_5$ is H, and $R_6$ is hydroxyalkyl;

(o) $R_1$ is H, $R_2$ is H, $R_3$ is H, $R_4$ is H, $R_5$ is H, and $R_6$ is alkylaminoalkyl;

(p) $R_1$ is H, $R_2$ is loweralkyl, $R_3$ is H, $R_4$ is H, $R_5$ is H, and $R_6$ is loweralkyl; and (q) $R_1$ is H, $R_2$ is H, $R_3$ is H, $R_4$ is H, two $R_5$ groups together represent $C_2$ alkyl, and $R_6$ is loweralkyl.

18. The method according to claim 13, wherein said compound of Formula (I) is selected from the group consisting of 2,5-bis(4-guanylphenyl)furan, 2,5-bis(4-guanylphenyl)-3,4-dimethylfuran, 2,5-di-p[2(3,4,5,6-tetrahydropyrimidyl)phenyl]furan, 2,5-bis[4-(2-imidazolinyl)phenyl]furan, 2,5-[bis{4-(2-tetrahydropyrimidinyl)}phenyl]3-p(tolyloxy)furan, 2,5-[bis{4-(2-imidazolinyl)}phenyl]3-p(tolyloxy) furan, 2,5-bis{4-[2-(N-2-hydroxyethyl)imidazolinyl]-phenyl}furan, 2,5-bis[4-(N-isopropylamidino)phenyl]furan, 2,5-bis{4-[3-(dimethylaminopropyl)amidino]phenyl}furan, 2,5-bis-{4-[N-(3-aminopropyl)amidino]phenyl}furan, 2,5-bis[2-(imidzaolinyl)phenyl]-3,4-bis(methoxymethyl)-furan, 2,5-bis[4-N-(dimethylaminoethyl)guanyl]phenylfuran, 2,5-bis-{4-[(N-2-hydroxyethyl)guanyl]phenyl}furan, 2,5-bis-[4-N-(cyclopropylguanyl)phenyl]furan, 2,5-bis-[4-(N,N-diethylaminopropyl)guanyl]phenylfuran, 2,5-bis-{4-[2-(N-ethylimidazolinyl)]phenyl}furan, 2,5-bis-{4-[N-( 3-pentylguanyl)amindino]}phenylfuran, 2,5-bis-[4-(2-imidazolinyl)phenyl]-3-methoxyfuran, 2,5-bis[4-(N-isopropylamidino)phenyl]-3-methylfuran, and the pharmaceutically acceptable salts thereof.

19. A compound according to Formula (I):

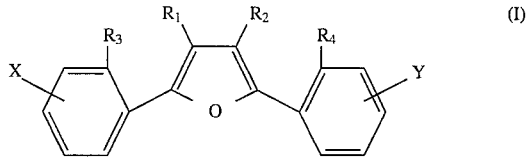

wherein:

X and Y are located in the para position and are each

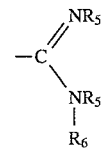

and wherein said compounds of Formula (I) are selected from the group consisting of compounds wherein:

(a) $R_1$ is H, $R_2$ is H or loweralkyl, $R_3$ is H, $R_4$ is H, $R_5$ is H, and $R_6$ is isoalkyl;

(b) $R_1$ is H, $R_2$ is H, $R_3$ is H, $R_4$ is H, $R_5$ is H, and $R_6$ is $C_3$-$C_8$ alkoxyalkyl;

(c) $R_1$ is H, $R_2$ is H or loweralkyl, $R_3$ is H, $R_4$ is H, $R_5$ is H, and $R_6$ is propylhydroxy, butylhydroxy, pentylhydroxy, and hexylhydroxy;

(d) $R_1$ is H, $R_2$ is H or loweralkyl, $R_3$ is H, $R_4$ is H, $R_5$ is H, and $R_6$ is propoxyethyl;

(f) $R_1$ is H, $R_2$ is H or loweralkyl, $R_3$ is H, $R_4$ is H, $R_5$ is H, and $R_6$ is propoxyisopropyl;

(g) $R_1$ is H, $R_2$ is H or loweralkyl, $R_3$ is H, $R_4$ is H, $R_5$ is H, and $R_6$ is aryl or alkylaryl; and (h) $R_1$ is H, $R_2$ is H or loweralkyl, $R_3$ is H, $R_4$ is H, $R_5$ is H, and $R_6$ is alkylcycloalkyl;

and phamaceutically acceptable salts thereof.

* * * * *